US010480125B2

(12) United States Patent
Kramer et al.

(10) Patent No.: US 10,480,125 B2
(45) Date of Patent: Nov. 19, 2019

(54) BIOCIDAL COMPOSITIONS

(75) Inventors: Jeffrey Kramer, Snellville, GA (US); Suresh Patel, Manchester (GB); Sylvie Gascoigne, Davyhulme (GB)

(73) Assignee: BWA WATER ADDITIVES UK LIMITED, Manchester (GB)

( * ) Notice: Subject to any disclaimer, the term of this patent is extended or adjusted under 35 U.S.C. 154(b) by 1354 days.

(21) Appl. No.: 12/399,300

(22) Filed: Mar. 6, 2009

(65) Prior Publication Data

US 2010/0226874 A1  Sep. 9, 2010

(51) Int. Cl.
  *D21C 9/08* (2006.01)
  *A01N 57/34* (2006.01)
  *D21H 21/36* (2006.01)
  *C02F 1/50* (2006.01)
  *A01N 33/12* (2006.01)

(52) U.S. Cl.
  CPC .............. *D21C 9/08* (2013.01); *A01N 33/12* (2013.01); *A01N 57/34* (2013.01); *D21H 21/36* (2013.01); *A01N 2300/00* (2013.01); *C02F 1/50* (2013.01); *F28F 2265/20* (2013.01)

(58) Field of Classification Search
  CPC ........ A01N 57/36; A01N 25/10; A01N 33/12; A01N 2300/00; A01N 57/34; A01P 1/00; C02F 1/50; D21C 9/08; D21H 21/36; F28F 2265/20
  See application file for complete search history.

(56) References Cited

U.S. PATENT DOCUMENTS

| | | | | |
|---|---|---|---|---|
| 3,281,365 A * | 10/1966 | Moedritzer | ............... | C07F 9/54 424/70.23 |
| 4,835,143 A | 5/1989 | Donofrio et al. | | |
| 5,102,874 A | 4/1992 | Lintner et al. | | |
| 5,376,731 A | 12/1994 | Kerr et al. | | |
| 5,741,757 A * | 4/1998 | Cooper | ................... | A01N 57/20 504/153 |
| 6,241,898 B1 * | 6/2001 | Wright et al. | ................ | 210/764 |
| 2010/0200239 A1 | 8/2010 | Aften | | |

FOREIGN PATENT DOCUMENTS

| | | | |
|---|---|---|---|
| EP | 0479465 A2 | | 4/1992 |
| EP | 0681995 A2 | | 11/1995 |
| GB | 2 354 771 A | * | 4/2001 |
| JP | 10-273408 A | * | 10/1998 |
| WO | WO199104668 | | 4/1991 |
| WO | WO 2005/123607 A1 | * | 12/2005 |
| WO | WO2010100470 | | 9/2010 |

OTHER PUBLICATIONS

Bellacide 303, Product Information, http://www.wateradditives.com/Repository/Files/BWA_Bellacide_303_GP_WF_-_AsiaPac_0.pdf.*

Bellacide 303, Technical Data, http://www.wateradditives.com/Repository/Files/BWA_Bellacide_303_TI_WF_AsiaPac.pdf.*
Bellacide 303 product label, http://www.kellysolutions.com/erenewals/documentsubmit/KellyData%5COK%5Cpesticide%5CProduct%20Label%5C83451%5C83451-20%5C83451-20_Bellacide_303_6_16_2011_2_54_43_PM.pdf.*
PTO translation of JP 10-273408, published Oct. 13, 1998.*

(Continued)

*Primary Examiner* — John Pak
*Assistant Examiner* — Nathan W Schlientz
(74) *Attorney, Agent, or Firm* — Kilpatrick Townsend & Stockton LLP

(57) ABSTRACT

Embodiments of the present subject matter provide a biocidal composition comprising an aqueous mixture of (a) a phosphonium compound and (b) a polymeric ammonium compound, wherein the weight ratio of compound (a) to compound (b) is from 0.2:1 to 20:1, and wherein the phosphonium compound (a) has formula:

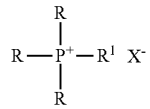

wherein each R is independently a $C_1$-$C_6$ alkyl group which is unsubstituted or substituted by a cyano, hydroxyl, esterified hydroxyl or aryl group;

$R^1$ represents a $C_8$-$C_{18}$ alkyl group which is substituted or unsubstituted; and X represents either chlorine or bromine; and wherein the polymeric ammonium compound (b) comprises the repeat unit:

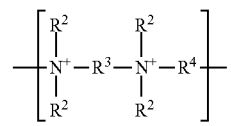

wherein each $R^2$ is independently a $C_1$-$C_2$ alkyl group which is substituted or unsubstituted;

$R^3$ represents a $C_2$-$C_{18}$ alkyl or alkenyl group which is substituted or unsubstituted; and $R^4$ represents a $C_2$-$C_{18}$ alkyl or alkenyl group which is substituted or unsubstituted, a diethyl ether group, an isopropanol group, a N,N-dipropylurea group, or a 2-butene group.

In some embodiments, the biocidal composition has a synergy index (SI) of less than 1 in relation to the effect of the composition on the inhibition of growth of biological organisms.

25 Claims, No Drawings

(56) References Cited

OTHER PUBLICATIONS

Kull, et al., 'Mixtures of Quaternary Ammonium Compounds and Long-chain Fatty Acids as Antifungal Agents,' *Applied Microbiology*, 9:538-541 (1961).
Rembaum, 'Biological Activity of Ionene Polymers,' Applied Polymer Symposium, J. Wiley & Sons, 22:299-317 (1973).
International Search Report dated Mar. 8, 2011 in related Application No. PCT/GB2010/050342.
May, O.W. Ed—Block S.S: "Polymeric Antimicrobial Agents," Disinfectants and Antiseptics, Philadelphia, Lea & Febiger, US, pp. 322-333 (1991).
U.S. Appl. No. 14/513,693, filed Oct. 14, 2014, Kramer.
U.S. Appl. No. 14/513,735, filed Oct. 14, 2014, Kramer.
U.S. Appl. No. 14/513,768, filed Oct. 14, 2014, Kramer.
U.S. Appl. No. 14/673,419, filed Mar. 30, 2015, Kramer et al.
U.S. Appl. No. 14/840,674, filed Aug. 31, 2015, Kramer.
U.S. Appl. No. 14/870,951, filed Sep. 30, 2015, Kramer.
U.S. Appl. No. 14/872,399, filed Oct. 1, 2015, Kramer.
U.S. Appl. No. 14/874,686, filed Oct. 5, 2015, Kramer et al.
U.S. Appl. No. 14/878,240, filed Oct. 8, 2015, Kramer et al.

\* cited by examiner

BIOCIDAL COMPOSITIONS

FIELD OF THE INVENTION

The present invention relates to biocidal compositions, to methods of treating aqueous systems to inhibit growth of micro-organisms and to apparatus comprising treated aqueous systems.

BACKGROUND TO THE INVENTION

The presence and growth of microorganisms in aqueous systems, especially industrial water systems, is a concern. Examples of industrial water systems where microorganisms are a concern include cooling water systems, pulping and papermaking systems and oil and gas field water systems.

The presence of microorganisms in industrial water systems may result in the formation of deposits on system surfaces. These deposits or slime can give rise to various problems. In cooling water systems, slime may restrict water flow, reduce heat transfer efficiency, cause corrosion and may be aesthetically unappealing especially if algae are present due to their visible green pigmentation. Corrosion can also occur in industrial water systems in the absence of visible slime through the action of microorganisms.

In pulp and paper mill systems, slime formed by microorganisms may cause fouling, plugging, or corrosion of the system. The slime may also break loose and become entrained in the paper produced causing blemishes, holes, tears, and odour in the finished product. The end result may therefore be unusable product and wasted output.

Slime can also be a problem in oil and gas field water systems and may cause energy losses due to increased fluid frictional resistance, formation plugging and corrosion. The slime may harbour a mixture of aerobic and anaerobic bacteria that are responsible for the production of hydrogen sulfide gas. The hydrogen sulfide may cause souring of oil and gas which may reduce the quality of these products and increase treatment costs.

*Pseudomonas aeruginosa* bacteria are commonly present in air, water and soil. These bacteria continually contaminate open cooling water systems, pulping and papermaking systems and oil and gas field water systems and are among the most common slime formers. Slime may be viewed as being a mass of cells stuck together by the cementing action of the gelatinous secretions around each cell. The slime entraps other debris, restricts water flow and heat transfer and may serve as a site for corrosion.

*Chlorella vulgaris* algae are also commonly present in air, water and soil. These algae continually contaminate open cooling water systems and their growth turns the water and surfaces in these systems green. They also provide a food source for bacteria, which can stimulate slime formation, and protozoa which can harbour the pathogenic bacterium *Legionella pneumophila*.

A known method of controlling microbial growth in industrial systems is to use biocides. While biocides are known to inhibit microbial growth the biocidal effect is generally of limited duration. The effectiveness of known biocides may be rapidly reduced as a result of exposure to negative influences. Negative influences may include temperature, pH or reaction with ingredients present in the system which neutralizes their biocidal effect. Therefore, the use of such biocides may involve continuous or frequent addition and their application at multiple sites or zones in the system to be treated. The cost of the biocide treatment and the labour costs associated with the application of known biocides may therefore be significant.

Known biocides are also highly toxic in the quantities known to be required for effective control of microbial populations. As a result, the amount of biocides that can be safely discharged into the environment may be limited by environmental regulations. Therefore, the need exists for improved methods for controlling microbial growth in industrial water systems.

One method of treating water is embodied in U.S. Pat. No. 4,835,143 issued May 30, 1989 to Donofrio et al. The Donofrio reference teaches the use of a composition of tri-n-butyl n-tetradecyl phosphonium chloride (hereinafter "TTPC") and an n-alkyl (50% $C_{14}$, 40% $C_{12}$, 10% $C_{16}$) dimethyl benzyl ammonium chloride (hereinafter "quat 1") to industrial process water to control the growth of microorganisms. A second method is embodied in U.S. Pat. No. 5,102,874 issued Apr. 7, 1992 to Lintner et al. The Lintner reference teaches the use of a composition of TTPC and an n-alkyl (70% $C_{12}$, 30% $C_{14}$) dimethyl benzyl ammonium chloride (hereinafter "quat 2") to industrial process water to control the growth of microorganisms. Both these methods utilize monomeric n-alkyl dimethyl benzyl ammonium chloride biocides in combination with the TTPC to provide the biocidal effect though TTPC does have biocidal activity alone.

There are also known many alternatives to the above mentioned monomeric n-alkyl dimethyl benzyl ammonium chloride biocides which can be used with TTPC to treat water. For example, Bromonitropropanediol, Alkydimethylbenzyl ammonium chloride, Methylene bisthiocyanate, Decylthioethaneamine, Dodecylguanidine hydrochloride, Dimethylphenylflurodichloromethylthio sulfamide, Bromonitrostyrene, Dimethyl thiadiazine thione, Tributyl tin oxide, Isothiazolone, Diiodomethyltolysulfone, Bromonitroethenyl furan, Glutaraldehyde and Hydrazine are all non-oxidising biocides which are known for use with TTPC. In addition, Bromochlorodimethyl hydantoin, Sodium hypochlorite, Trichloroisocyanuric acid, Sodium hypobromite and Peroxygen compounds are all oxidising biocides which are known for use with TTPC. In addition there are of course many biocides, including some of those listed above, which are known for use without TTPC. Polymeric ammonium chloride compounds with biocidal activity have for example been described by Rembaum in Applied Polymer Symposium, J. Wiley & Sons, No. 22, pp. 299-317.

As noted above, known biocides have a number of limitations including the large quantities of biocides which typically have to be used to achieve the desired biocidal effect and the potential harmful effects on the environment of biocides and therefore reducing the amount necessary for control and thus the quantity released to the environment has many benefits.

Accordingly, the present invention aims to address at least one disadvantage associated with the prior art whether discussed herein or otherwise.

SUMMARY OF THE INVENTION

According to a first aspect of the present invention there is provided a biocidal composition comprising an aqueous mixture of (a) a phosphonium compound and (b) a polymeric ammonium compound; wherein the weight ratio of compound (a) to compound (b) is from 0.2:1 to 20:1; and wherein the phosphonium compound (a) has formula:

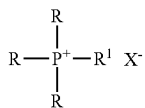

wherein each R is independently a $C_1$-$C_6$ alkyl group which is unsubstituted or substituted by a cyano, hydroxyl, esterified hydroxyl or aryl group;

$R^1$ represents a $C_8$-$C_{18}$ alkyl group which is substituted or unsubstituted; and X represents either chlorine or bromine; and wherein the polymeric ammonium compound (b) comprises the repeat unit:

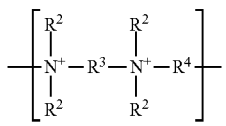

wherein each $R^2$ is independently a $C_1$-$C_2$ alkyl group which is substituted or unsubstituted;

$R^3$ represents a $C_2$-$C_{18}$ alkyl or alkenyl group which is substituted or unsubstituted; and $R^4$ represents a $C_2$-$C_{18}$ alkyl or alkenyl group which is substituted or unsubstituted, a diethyl ether group, an isopropanol group, a N,N-dipropylurea group, or a 2-butene group.

Suitably, the polymeric ammonium compound comprises n repeat units where n is from 2 to 40. Suitably n is 10-30. Suitably, n is 15-25. Suitably, n is 20. Suitably, the polymeric ammonium compound comprises sufficient counter-ions to balance the charge. Suitably, the counter-ions comprise singly charged ions, suitably halides. Suitably, the polymeric ammonium compound comprises 2n counter-ions. Suitably, the polymeric ammonium compound comprises chloride and/or bromide counter-ions.

Suitably, the polymeric ammonium compound (b) has formula:

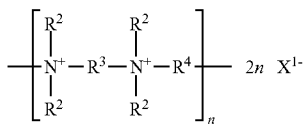

wherein each $R^2$ is independently a $C_1$-$C_2$ alkyl group which is substituted or unsubstituted;

$R^3$ represents a $C_2$-$C_{18}$ alkyl or alkenyl group which is substituted or unsubstituted;

$R^4$ represents a $C_2$-$C_{18}$ alkyl or alkenyl group which is substituted or unsubstituted, a diethyl ether group, an isopropanol group, a N,N-dipropylurea group, or a 2-butene group;

$X^1$ represents either chlorine or bromine; and
n is 2-40.

Suitably, the weight ratio of compound (a) to compound (b) is from 0.5:1 to 10:1. Suitably, the weight ratio of compound (a) to compound (b) is from 0.5:1 to 5:1. Suitably, the weight ratio of compound (a) to compound (b) is from 1:1 to 2:1. Suitably, the weight ratio of compound (a) to compound (b) is from 1:1 to 1.5:1, the weight ratio may for example be around 1.5:1. Suitably, the weight ratio of compound (a) to compound (b) is from 1.15:1 to 1.30:1, the weight ratio may for example be 1.25:1. The weight ratio of compound (a) to compound (b) may be from 2:1 to 5:1. The weight ratio of compound (a) to compound (b) may be from 2.5:1 to 4:1, the weight ratio may for example be around 4:1. The weight ratio of compound (a) to compound (b) may be from 3.1:1 to 3.5:1, the weight ratio may for example be 3.5:1

Suitably, by "biocidal composition" it is meant a composition which has a biocidal activity such that it inhibits the growth of biological organisms, preferably micro-organisms such as bacteria, fungi and/or algae.

Suitably, in use, the biocidal composition inhibits the growth of biological organisms. Suitably, in use, the biocidal composition inhibits the growth of micro-organisms. Suitably, the biocidal composition is effective against bacteria, fungi and/or algae. The biocidal composition may be effective against gram-positive aerobic bacteria, gram-positive facultative aerobic bacteria, gram-negative aerobic bacteria, gram-negative facultative aerobic bacteria, and/or gram-negative anaerobic bacteria. The biocidal composition may be effective against mold and/or yeast. The biocide may be effective against blue green algae and/or green algae. Suitably, the biocidal composition is effective against gram-negative aerobic bacteria and green algae. Suitably, the biocidal composition is effective in controlling the growth of *Pseudomonas aeruginosa* bacteria in an aqueous system. Suitably, the biocidal composition is effective in controlling the growth of *Chlorella vulgaris* algae in an aqueous system. Both *Pseudomonas aeruginosa* and *Chlorella vulgaris* are indicator organisms in industrial water systems and are commonly used as model organisms in laboratory evaluations of biocides.

Suitably, the biocidal composition comprises a synergistic mixture of compounds (a) and (b). Suitably, by "synergistic mixture" it is meant that the mixture of compounds (a) and (b) has a synergistic effect on the inhibition of growth of one or more biological organisms, preferably micro-organisms such as bacteria, fungi and/or algae.

Suitably, the biocidal composition has a synergy index (SI) of less than 1 in relation to the effect of the composition on the growth of one or more micro-organisms. Suitably, the biocidal composition has a synergy index (SI) of less than 1 in relation to the effect of the composition on the inhibition of growth of one or more bacteria. Suitably, the biocidal composition has a synergy index (SI) of less than 1 in relation to the effect of the composition on the inhibition of growth of *Pseudomonas aeruginosa* bacteria.

Suitably, synergy is determined by the method described by S. C. Kull et al. in *Applied Microbiology*, vol. 9, pages 538-541 (1961) using the relationship:

$$Q_a/Q_A + Q_b/Q_B = \text{synergy index(SI)}$$

where:

$Q_A$=quantity of compound (a), acting alone, producing an end point $Q_B$=quantity of compound (b), acting alone, producing an end point $Q_a$=quantity of compound (a) in mixture, producing an end point $Q_b$=quantity of compound (b) in mixture, producing an end point <1, it indicates synergy Suitably, if the synergy index (SI) is: 1, it indicates additivity >1, it indicates antagonism Suitably, the endpoint is determined by a given reduction in viable organisms. Suitably, an end point of 1 or 4 $\log_{10}$ reduction in viable organisms after 1 hour contact time is selected for calculating synergy.

Where compound (a) is employed in the form of an aqueous composition of said compound and water (composition A) and compound (b) is also employed in the form of an aqueous composition of said compound and water (composition B) it may be convenient to calculate synergy using the following values:

$Q_A$=quantity of composition A, acting alone, producing an end point $Q_B$=quantity of composition B, acting alone, producing an end point $Q_a$=quantity of composition A in mixture, producing an end point $Q_b$=quantity of composition B in mixture, producing an end point The biocidal composition may comprise one or more phosphonium compounds (a). Suitably, the biocidal composition comprises a single type of phosphonium compound (a).

Suitably, the biocidal composition comprises a phosphonium compound (a) having formula:

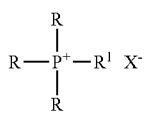

wherein each R is independently a $C_1$-$C_6$ alkyl group which is unsubstituted or substituted by a cyano, hydroxyl, esterified hydroxyl or aryl group;

$R^1$ represents a $C_8$-$C_{18}$ alkyl group; and

X represents either chlorine or bromine.

Suitably, each R is a $C_1$-$C_6$ alkyl group. Suitably, each R is a $C_3$-$C_5$ alkyl group. Suitably each R is a butyl group.

Suitably $R^1$ represents a $C_8$-$C_{18}$ alkyl group. Suitably, $R^1$ is a $C_{12}$-$C_{16}$ alkyl group. Suitably, $R^1$ is a tetradecyl group.

Suitably, X is chlorine.

Suitably, the biocidal composition comprises tri n-butyl n-tetradecyl phosphonium chloride (hereafter "TTPC"). Suitably, compound (a) comprises TTPC. Suitably, compound (a) consists of TTPC. TTPC is available from BWA Water Additives and is sold under the trade name Bellacide 350 (an aqueous composition of TTPC and water consisting of water and 50% by weight of TTPC) and Bellacide 355 (an aqueous composition of TTPC and water consisting of water and 5% by weight of TTPC).

The biocidal composition may comprise one or more polymeric ammonium compounds (b). Suitably, the biocidal composition comprises a single type of polymeric ammonium compound (b).

Suitably, the biocidal composition comprises a polymeric ammonium compound (b) having formula:

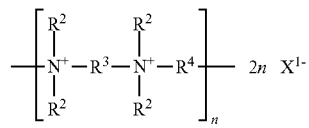

wherein each $R^2$ is independently a methyl group;

$R^3$ represents a $C_2$-$C_{12}$ alkyl group;

$R^4$ represents a $C_2$-$C_{12}$ alkyl group, a diethyl ether group, an isopropanol group or a N,N-dipropylurea group;

$X^1$ represents either chlorine or bromine; and n is 2-40.

Suitably, each $R^2$ is independently a methyl group.

Suitably, $R^3$ represents a $C_2$-$C_{12}$ alkyl group which is substituted or unsubstituted, suitably unsubstituted. Suitably, $R^3$ represents a $C_2$-$C_{12}$ alkyl group. Suitably, $R^3$ is a $C_2$-$C_4$ alkyl group. Suitably, $R^3$ is a $C_2$ alkyl group.

Suitably, $R^4$ represents a $C_2$-$C_{12}$ alkyl group which is substituted or unsubstituted, suitably unsubstituted. Suitably, $R^4$ represents a $C_2$-$C_{12}$ alkyl group, a diethyl ether group, an isopropanol group or a N,N-dipropylurea group. Suitably, $R^4$ represents a diethyl ether group.

Suitably, $X^1$ is chlorine.

Suitably, n is 10-30. Suitably, n is 15-25. Suitably, n is 20.

Suitably, the biocidal composition comprises Poly[oxyethylene(dimethylimino)ethylene(dimethylimino)ethylene dichloride] (hereafter "polyquat"). Polyquat is commercially available from various sources. For instance, it is sold under the trade name WSCP (an aqueous composition of polyquat and water consisting of water and 60% by weight of polyquat) as well as other trade names from Buckman Laboratories.

Suitably, compound (b) comprises Poly[oxyethylene(dimethylimino)ethylene(dimethylimino)ethylene dichloride].

Suitably, compound (b) consists of Poly[oxyethylene(dimethylimino)ethylene(dimethylimino)ethylene dichloride].

The biocidal composition may comprise α-4-[1-tris(2-hydroxyethyl)ammonium chloride-2-butenyl]poly[1-dimethylammonium chloride-2-butenyl]-ω-tris(2-hydroxyethyl) ammonium chloride.

The biocidal composition may further comprise a stabilising agent. Suitably, the biocidal composition comprises a hydrotrope.

Suitably, the hydrotrope comprises an amphoteric surfactant. Suitably, the hydrotrope is selected from the group consisting of alkyl ampho- or iminocarboxylate amphoteric surfactants. Suitably, the hydrotrope is selected from the group consisting of alkyl ampho- or iminodicarboxylate amphoteric surfactants. Suitably, the hydrotrope is selected from the group consisting of alkyl iminodipropionate amphoteric surfactants.

Suitably, the biocidal composition comprises one or more hydrotropes in a total amount of between 0.1% and 50% by weight of the composition. Suitably, the biocidal composition comprises one or more hydrotropes in an amount of between 0.3% and 35% by weight of the composition. Suitably, the biocidal composition comprises an alkyl iminodipropionate amphoteric surfactant in an amount of between 0.1% and 50% by weight of the composition, for example in an amount of between 0.3% and 35% by weight.

Suitably, the hydrotrope comprises an alkyl iminodipropionate amphoteric surfactant wherein the alkyl group is selected from the group consisting of 2-ethylhexyl-, octyl-, decyloxypropyl-, dodecyl-, coco- or tallow.

Suitably, the biocidal composition comprises one or more hydrotropes in a total amount of between 3% and 21% by weight of the composition, for example between 7% and 14% by weight. Suitably, the biocidal composition comprises an alkyl iminodipropionate amphoteric surfactant in an amount of between 3% and 21% by weight of the composition, for example between 7% and 14% by weight.

Suitably, the biocidal composition comprises compound (a) and compound (b) in a combined amount of between 1% and 100% by weight of the composition. Suitably, the biocidal composition comprises compound (a) and compound (b) in a combined amount of between 50% and 99.5% by weight of the composition. The composition may for example comprise compound (a) and compound (b) in a combined amount of between 70% and 95% by weight of the composition.

The biocidal composition may be prepared by combining an aqueous composition of component (a) with an aqueous composition of component (b) and optionally additional water. Suitably, compound (a) is used in the form of an aqueous composition comprising between 30% and 70% by weight of compound (a), for example around 50% by weight. Suitably, compound (b) is used in the form of an aqueous composition comprising between 40% and 80% by weight of compound (b), for example around 60% by weight.

Suitably, the biocidal composition comprises water in an amount of between 0% and 99% by weight of the composition. Suitably, the biocidal composition comprises water in an amount of no more than 50% by weight of the composition, suitably no more than 30% by weight. The composition may for example comprise water in an amount of between 0% and 20% by weight of the composition.

Suitably, the biocidal composition consists of one or more types of compound (a), one or more types of compound (b), one or more hydrotropes and water.

Suitably, the biocidal composition consists of a single type of compound (a), a single type of compound (b), a hydrotrope and water.

Surprisingly, the present inventor has found that mixtures of compounds (a) and (b) such as mixtures of tri-n-butyl n-tetradecyl phosphonium chloride (TTPC) and a poly[oxyethylene(dimethyliminio)ethylene(dimethyliminio)ethylene dichloride](polyquat) are especially efficacious in controlling the growth of bacterial and algal microbes. The efficacy in relation to *Pseudomonas aeruginosa* and *Chlorella vulgaris* species is marked with certain selections of amounts and ratios of components and there is an unexpected synergistic relationship. It has been found that compositions having a weight ratio of compound (a):compound (b) of from 1:1 to 5:1 may be particularly beneficial and may have a marked synergy in relation to *Pseudomonas aeruginosa*.

Surprisingly, the present inventor has also found that the formulation of stable compositions is possible by selection of appropriate amounts and ratios of components. Surprisingly it has been found that compositions which are stable at a broad range of temperatures can be formulated.

According to a second aspect of the present invention there is provided a biocidal composition comprising an aqueous mixture of (a) phosphonium chloride compound; and (b) a polymeric ammonium compound.

Suitably, the polymeric ammonium compound (b) comprises a polymeric ammonium chloride compound.

Suitably, the biocidal composition comprises an aqueous mixture of (a) tri-n-butyl n-tetradecyl phosphonium chloride (hereafter "TTPC") and (b) a polymeric ammonium chloride compound.

The polymeric ammonium compound (b) may comprise a compound having a formula as defined in relation to compound (b) in the first aspect. Suitably, the polymeric ammonium compound (b) comprises poly[oxyethylene(dimethylimino)ethylene(dimethylimino)ethylene dichloride. Alternatively, the polymeric ammonium compound (b) may comprise α-4-[1-tris(2-hydroxyethyl)ammonium chloride-2-butenyl]poly[1-dimethylammonium chloride-2-butenyl]-ω-tris(2-hydroxyethyl)ammonium chloride.

Suitably, the weight ratio of compound (a) to compound (b) is from 0.2:1 to 20:1.

Suitably, the weight ratio of compound (a) to compound (b) is from 0.5:1 to 10:1. Suitably, the weight ratio of compound (a) to compound (b) is from 0.5:1 to 5:1. Suitably, the weight ratio of compound (a) to compound (b) is from 1:1 to 2:1. Suitably, the weight ratio of compound (a) to compound (b) is from 1:1 to 1.5:1, the weight ratio may for example be around 1.5:1. Suitably, the weight ratio of compound (a) to compound (b) is from 1.15:1 to 1.30:1, the weight ratio may for example be 1.25:1. The weight ratio of compound (a) to compound (b) may be from 2:1 to 5:1, The weight ratio of compound (a) to compound (b) may be from 2.5:1 to 4:1, the weight ratio may for example be around 4:1. The weight ratio of compound (a) to compound (b) may be from 3.1:1 to 3.5:1, the weight ratio may for example be 3.5:1.

Suitably, the biocidal composition comprises a synergistic mixture of compounds (a) and (b).

Suitably, there is provided a biocidal composition comprising an aqueous mixture of (a) tri-n-butyl n-tetradecyl phosphonium chloride (hereafter "TTPC") and (b) poly[oxyethylene(dimethylimino)ethylene(dimethylimino)ethylene dichloride (hereafter "polyquat"); and wherein the weight ratio of (a) to (b) is from 0.2:1 to 20:1.

The biocidal composition may further comprise a stabilising agent. Suitably, the biocidal composition comprises a hydrotrope.

Suitably, the hydrotrope comprises an amphoteric surfactant. Suitably, the hydrotrope is selected from the group consisting of alkyl iminodipropionate amphoteric surfactants.

Suitably, the biocidal composition comprises one or more hydrotropes in a total amount of between 0.1% and 50% by weight of the composition, for example between 0.3% and 35% by weight. Suitably, the biocidal composition comprises an alkyl iminodipropionate amphoteric surfactant in an amount of between 0.1% and 50% by weight of the composition, for example between 0.35% and 35% by weight.

Suitably, the biocidal composition comprises compound (a) and compound (b) in a combined amount of between 1% and 100% by weight of the composition. Suitably, the biocidal composition comprises compound (a) and compound (b) in a combined amount of between 50% and 99.5% by weight of the composition. The composition may for example comprise compound (a) and compound (b) in a combined amount of between 70% and 95% by weight of the composition.

The biocidal composition may be prepared by combining an aqueous composition of component (a) with an aqueous composition of component (b) and optionally additional water. Suitably, compound (a) is used in the form of an aqueous composition comprising between 30% and 70% by weight of compound (a), for example around 50% by weight. Suitably, compound (b) is used in the form of an aqueous composition comprising between 40% and 80% by weight of compound (b), for example around 60% by weight.

Suitably, the biocidal composition comprises water in an amount of between 0% and 99% by weight of the composition. Suitably, the biocidal composition comprises water in an amount of no more than 50% by weight of the composition, suitably no more than 30% by weight. The composition may for example comprise water in an amount of between 0% and 20% by weight of the composition.

Suitably, the biocidal composition consists of one or more types of compound (a), one or more types of compound (b), one or more hydrotropes and water.

Suitably, the biocidal composition consists of a single type of compound (a), a single type of compound (b), a hydrotrope and water.

The composition of the second aspect may comprise any feature as described in relation to the first aspect except where such features are mutually exclusive.

According to a third aspect of the present invention there is provided a method of treating an aqueous system to inhibit growth of one or more micro-organisms therein; wherein the method comprises adding (a) a phosphonium compound and (b) a polymeric ammonium compound to an aqueous system such that the weight ratio of compound (a) to compound (b) is from 0.2:1 to 20:1; and wherein
the phosphonium compound (a) has formula:

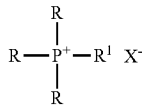

wherein each R is independently a $C_1$-$C_6$ alkyl group which is unsubstituted or substituted by a cyano, hydroxyl, esterified hydroxyl or aryl group;
$R^1$ represents a $C_8$-$C_{18}$ alkyl group which is substituted or unsubstituted; and
X represents either chlorine or bromine; and wherein
the polymeric ammonium compound (b) comprises the repeat unit:

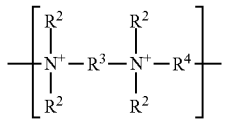

wherein each R is independently a $C_1$-$C_2$ alkyl group which is substituted or unsubstituted;
$R^3$ represents a $C_2$-$C_{18}$ alkyl or alkenyl group which is substituted or unsubstituted; and
$R^4$ represents a $C_2$-$C_{18}$ alkyl or alkenyl group which is substituted or unsubstituted, a diethyl ether group, an isopropanol group, a N,N-dipropylurea group, or a 2-butene group.

Suitably, the polymeric ammonium compound comprises n repeat units where n is from 2 to 40. Suitably n is 10-30. Suitably, n is 15-25. Suitably, n is 20. Suitably, the polymeric ammonium compound comprises sufficient counter-ions to balance the charge, Suitably, the counter-ions comprise singly charged ions, suitably halides. Suitably, the polymeric ammonium compound comprises 2n counter-ions. Suitably, the polymeric ammonium compound comprises chloride and/or bromide counter-ions.

Suitably, the polymeric ammonium compound (b) has formula:

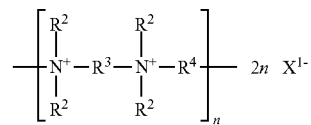

wherein each R is independently a $C_1$-$C_2$ alkyl group which is substituted or unsubstituted;
$R^3$ represents a $C_2$-$C_{18}$ alkyl or alkenyl group which is substituted or unsubstituted;
$R^4$ represents a $C_2$-$C_{18}$ alkyl or alkenyl group which is substituted or unsubstituted, a diethyl ether group, an isopropanol group, a N,N-dipropylurea group or a 2-butene group;
$X^1$ represents either chlorine or bromine; and
n is 2-40.

The aqueous system to be treated may comprise constituents other than water. The aqueous system to be treated may alternatively consist of water. Suitably the aqueous system comprises a mixture of water and other constituents. The aqueous system may contain oil. The aqueous system may comprise an oil and water emulsion.

Suitably, the method comprises adding compound (a) and compound (b) to the aqueous system such that the weight ratio of compound (a) to compound (b) is from 0.5:1 to 10:1.

Suitably, the weight ratio of compound (a) to compound (b) is from 0.5:1 to 5:1. Suitably, the weight ratio of compound (a) to compound (b) is from 1:1 to 2:1. Suitably, the weight ratio of compound (a) to compound (b) is from 1:1 to 1.5:1, the weight ratio may for example be around 1.5:1. Suitably, the weight ratio of compound (a) to compound (b) is from 1.15:1 to 1.30:1, the weight ratio may for example be 1.25:1. The weight ratio of compound (a) to compound (b) may be from 2:1 to 5:1. The weight ratio of compound (a) to compound (b) may be from 2.5:1 to 4:1, the weight ratio may for example be around 4:1. The weight ratio of compound (a) to compound (b) may be from 3.1:1 to 3.5:1, the weight ratio may for example be 3.5:1

Suitably, the method comprises adding compound (a) and compound (b) to the aqueous system such that they are present in a combined amount of from 0.05 to 200 parts by weight per one million parts by weight of said aqueous system.

The method may comprise adding compound (a) and compound (b) to the aqueous system such that they are present in a combined amount of from 0.1 to 100 parts by weight per million parts by weight of said aqueous system. Suitably, the method comprises adding compound (a) and compound (b) to the aqueous system such that they are present in a combined amount of from 1 to 50 parts by weight per one million parts by weight of said aqueous system. Suitably, the method comprises adding compound (a) and compound (b) to the aqueous system such that they are present in a combined amount of from 2 to 30 parts by weight per one million parts by weight of said aqueous system.

Suitably, the method employs a synergistic mixture of compounds (a) and (b). Suitably, by "synergistic mixture" it is meant that the mixture of compounds (a) and (b) has a synergistic effect on the inhibition of growth of one or more biological organisms, preferably micro-organisms such as bacteria, fungi and/or algae.

Suitably, the aqueous mixture of compounds (a) and (b) has a synergy index (SI) of less than 1 in relation to the effect of the composition on the growth of one or more microorganisms.

Suitably, the method comprises adding compound (a) to compound (b) to the aqueous system such that the aqueous system comprises a synergistic mixture of compounds (a) and (b).

Suitably, the method comprises a method of inhibiting growth of bacteria, fungi and/or algae. The method may comprise a method of inhibiting growth of gram-positive aerobic bacteria, gram-positive facultative aerobic bacteria, gram-negative aerobic bacteria, gram-negative facultative aerobic bacteria, and/or gram-negative anaerobic bacteria. The method may comprise a method of inhibiting growth of mold and/or yeast. The method may comprise a method of inhibiting the growth of blue green algae and/or green algae. Suitably, the method comprises a method of inhibiting the growth of gram-negative aerobic bacteria and green algae. Suitably, the method comprises controlling the growth of *Pseudomonas aeruginosa* bacteria in an aqueous system. Suitably, the method comprises controlling the growth of *Chlorella vulgaris* algae in an aqueous system.

The method may employ one or more phosphonium compounds (a). Suitably, the method employs a single type of phosphonium compound (a).

Suitably, the method employs a phosphonium compound (a) having formula:

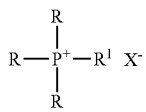

wherein each R is independently a $C_1$-$C_6$ alkyl group which is unsubstituted or substituted by a cyano, hydroxyl, esterified hydroxyl or aryl group;
$R^1$ represents a $C_8$-$C_{18}$ alkyl group; and
X represents either chlorine or bromine.

Suitably, each R is a $C_1$-$C_6$ alkyl group. Suitably, each R is a $C_3$-$C_5$ alkyl group. Suitably each R is a butyl group.

Suitably $R^1$ represents a $C_8$-$C_{18}$ alkyl group. Suitably, $R^1$ is a $C_{12}$-$C_{16}$ alkyl group. Suitably, $R^1$ is a tetradecyl group.

Suitably, X is chlorine.

Suitably, the method comprises adding tri n-butyl n-tetradecyl phosphonium chloride (hereafter "TTPC") to the aqueous system. Suitably, compound (a) comprises TTPC. Suitably, compound (a) consists of TTPC.

The method may employ one or more polymeric ammonium compounds (b). Suitably, the method employs a single type of polymeric ammonium compound (b).

Suitably, the method employs a polymeric ammonium compound (b) having formula:

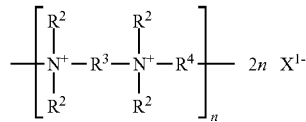

wherein each $R^2$ is independently a methyl group;
$R^3$ represents a $C_2$-$C_{12}$ alkyl group;
$R^4$ represents a $C_2$-$C_{12}$ alkyl group, a diethyl ether group, an isopropanol group or a N,N-dipropylurea group;
$X^1$ represents either chlorine or bromine; and
n is 2-40.

Suitably, each $R^2$ is independently a methyl group.
Suitably, $R_3$ represents a $C_2$-$C_{12}$ alkyl group. Suitably, $R^3$ is a $C_2$-$C_4$ alkyl group. Suitably, $R^3$ is a $C_2$ alkyl group.
Suitably, $R^4$ represents a $C_2$-$C_{12}$ alkyl group, a diethyl ether group, an isopropanol group or a N,N-dipropylurea group. Suitably, $R^4$ represents a diethyl ether group.
Suitably, $X^1$ is chlorine.
Suitably, n is 10-30. Suitably, n is 15-25. Suitably, n is 20.
Suitably, the method comprises adding Poly[oxyethylene (dimethylimino)ethylene(dimethylimino)ethylene dichloride] (hereafter "polyquat") to the aqueous system.
Suitably, compound (b) comprises Poly[oxyethylene(dimethylimino)ethylene(dimethylimino)ethylene dichloride].
Suitably, compound (b) consists of Poly[oxyethylene(dimethylimino)ethylene(dimethylimino)ethylene dichloride].
The method may comprise adding α-4-[1-tris(2-hydroxyethyl)ammonium chloride-2-butenyl]poly[1-dimethylammonium chloride-2-butenyl]-ω-tris(2-hydroxyethyl)ammonium chloride to the aqueous system.
Suitably, the method comprises adding compound (a) and compound (b) as a mixture to the aqueous system. Suitably, the method comprises adding a biocidal composition comprising compound (a) and compound (b) to the aqueous system. Alternatively, or in addition, the method may comprise mixing compound (a) and compound (b) and adding the mixture to the aqueous system. Alternatively, or in addition, the method may comprise adding compound (a) and compound (b) separately to the aqueous system and allowing or causing them to mix within the aqueous system.

Where the method comprises mixing compound (a) and compound (b) and adding the mixture to the aqueous system and/or adding compound (a) and compound (b) separately to the aqueous system and allowing or causing them to mix within the aqueous system then compounds (a) and (b) are preferably used in the form of aqueous compositions. Suitably, compound (a) is used in the form of an aqueous composition comprising between 30% and 70% by weight of compound (a), for example around 50% by weight. Suitably, compound (b) is used in the form of an aqueous composition comprising between 40% and 80% by weight of compound (b), for example around 60% by weight.

Where the method comprises adding a biocidal composition comprising compound (a) and compound (b) to the aqueous system then the biocidal composition preferably comprises an aqueous mixture of compounds (a) and (b). Suitably, the biocidal composition comprises compound (a) and compound (b) in a combined amount of between 1% and 99% by weight of the composition, for example between 30% and 80% by weight.

Suitably, the method comprises adding a biocidal composition according to the first aspect to the aqueous system. The method may comprise adding a biocidal composition according to the first aspect to water. The method may comprise a method of treating an industrial water system and may comprise adding a biocidal composition according to the first aspect to an industrial water system.

The method may comprise adding a biocidal composition according to the first aspect in an amount of between, 0.05 and 200 parts by weight of composition per one million parts by weight of said aqueous composition. The method may comprise adding a biocidal composition according to the first aspect in an amount of between 2 and 30 parts by weight of composition per one million parts by weight of said aqueous composition.

The method may comprise treating a cooling water system. The method may comprise treating a pulping and/or papermaking system. The method may comprise treating a oil and/or gas field water system. The method may comprise treating an aqueous system to control the growth of bacterial and/or algal microorganisms contained therein and/or which may become entrained in said system.

It has been found that the compositions and methods of utilisation of the present invention may in particular be efficacious in controlling the aerobic bacterium *Pseudomonas aeruginosa* and/or the green alga *Chlorella vulgaris*, which may populate aqueous systems.

Surprisingly, it has been found that when compounds (a) and (b) are mixed the resulting mixtures may pose a higher degree of biocidal activity than that of the individual ingredients comprising the mixture. Accordingly, it may be possible to produce a highly efficacious biocide. Because of the enhanced activity of the mixture, it may be possible for the total quantity of the biocidal treatment to be reduced. In addition, the high degree of biocidal activity which is provided by each of the ingredients may be exploited without use of higher concentrations of each. The combination of TTPC and polyquat may be particularly effective.

The method of the third aspect may comprise any feature as described in relation to one or more of the first and/or second aspects except where such features are mutually exclusive.

According to a fourth aspect of the present invention there is provided a method of treating an aqueous system to inhibit growth of one or more micro-organisms therein; wherein the method comprises adding (a) a phosphonium chloride compound and (b) a polymeric ammonium compound to the aqueous system.

Suitably, the polymeric ammonium compound (b) comprises a polymeric ammonium chloride compound.

The aqueous system to be treated may comprise constituents other than water. The aqueous system to be treated may alternatively consist of water. Suitably the aqueous system comprises a mixture of water and other constituents. The aqueous system may contain oil. The aqueous system may comprise an oil and water emulsion.

Suitably, the method comprises treating an aqueous system to inhibit growth of one or more micro-organisms therein, wherein the method comprises adding to the aqueous system:

(a) tri-n-butyl n-tetradecyl phosphonium chloride (hereafter "TTPC") and (b) a polymeric ammonium chloride compound.

The polymeric ammonium compound (b) may comprise a compound having a formula as defined in relation to compound (b) in the first aspect. Suitably, the polymeric ammonium compound (b) comprises poly[oxyethylene(dimethylimino)ethylene(dimethylimino)ethylene dichloride (hereafter "polyquat"). Alternatively, the polymeric ammonium compound (b) may comprise α-4-[1-tris(2-hydroxyethyl)ammonium chloride-2-butenyl]poly[1-dimethylammonium chloride-2-butenyl]-ω-tris (2-hydroxyethyl)ammonium chloride.

Suitably, the method comprises adding compound (a) and compound (b) to the aqueous system such that their weight ratio in the aqueous system is from 0.2:1 to 20:1.

Suitably, the method comprises adding compound (a) and compound (b) to the aqueous system such that the weight ratio of compound (a) to compound (b) is from 0.5:1 to 10:1.

Suitably, the weight ratio of compound (a) to compound (b) is from 0.5:1 to 5:1. Suitably, the weight ratio of compound (a) to compound (b) is from 1:1 to 2:1. Suitably, the weight ratio of compound (a) to compound (b) is from 1:1 to 1.5:1, the weight ratio may for example be around 1.5:1. Suitably, the weight ratio of compound (a) to compound (b) is from 1.15:1 to 1.30:1, the weight ratio may for example be 1.25:1. The weight ratio of compound (a) to compound (b) may be from 2:1 to 5:1. The weight ratio of compound (a) to compound (b) may be from 2.5:1 to 4:1, the weight ratio may for example be around 4:1. The weight ratio of compound (a) to compound (b) may be from 3.1:1 to 3.5:1, the weight ratio may for example be 3.5:1.

Suitably, the method comprises adding compound (a) and compound (b) to the aqueous system such that they are present in a combined amount of from 0.05 to 200 parts by weight per one million parts by weight of said aqueous system.

The method may comprise adding compound (a) and compound (b) to the aqueous system such that they are present in a combined amount of from 0.1 to 100 parts by weight per million parts by weight of said aqueous system. Suitably, the method comprises adding compound (a) and compound (b) to the aqueous system such that they are present in a combined amount of from 1 to 50 parts by weight per one million parts by weight of said aqueous system. Suitably, the method comprises adding compound (a) and compound (b) to the aqueous system such that they are present in a combined amount of from 2 to 30 parts by weight per one million parts by weight of said aqueous system.

Suitably, the method employs a synergistic mixture of compounds (a) and (b).

Suitably, there is provided a method of treating an aqueous system with a biocide, wherein the method comprises adding to the aqueous system (a) tri-n-butyl n-tetradecyl phosphonium chloride (hereafter "TTPC") and (b) poly[oxyethylene(dimethylimino)ethylene(dimethylimino)ethylene dichloride (hereafter "polyquat"); and wherein compound (a) and compound (b) are added to the aqueous system such that their weight ratio in the aqueous system is from 0.2:1 to 20:1.

Suitably, the method comprises adding compound (a) and compound (b) as a mixture to the aqueous system. Suitably, the method comprises adding a biocidal composition comprising compound (a) and compound (b) to the aqueous system. Alternatively, or in addition, the method may comprise mixing compound (a) and compound (b) and adding the mixture to the aqueous system. Alternatively, or in addition, the method may comprise adding compound (a) and compound (b) separately to the aqueous system and allowing or causing them to mix within the aqueous system.

Where the method comprises mixing compound (a) and compound (b) and adding the mixture to the aqueous system and/or adding compound (a) and compound (b) separately to the aqueous system and allowing or causing them to mix within the aqueous system then compounds (a) and (b) are preferably used in the form of aqueous compositions. Suitably, compound (a) is used in the form of an aqueous composition comprising between 30% and 70% by weight of compound (a), for example around 50% by weight. Suitably, compound (b) is used in the form of an aqueous composition comprising between 40% and 80% by weight of compound (b), for example around 60% by weight.

Where the method comprises adding a biocidal composition comprising compound (a) and compound (b) to the aqueous system then the biocidal composition preferably comprises an aqueous mixture of compounds (a) and (b). Suitably, the biocidal composition comprises compound (a) and compound (b) in a combined amount of between 1% and 99% by weight of the composition, for example between 30% and 80% by weight.

Suitably, the method comprises adding a biocidal composition according to the second aspect to the aqueous system. The method may comprise adding a biocidal composition according to the second aspect to water. The method may comprise a method of treating an industrial water system and may comprise adding a biocidal composition according to the second aspect to an industrial water system. The method may comprise adding a biocidal composition according to the second aspect in an amount of between 0.05 and 200 parts by weight of composition per one million parts by weight of said aqueous composition. The method may comprise adding a biocidal composition according to the second aspect in an amount of between 2 and 30 parts by weight of composition per one million parts by weight of said aqueous composition.

The method of the fourth aspect may comprise any feature as described in relation to the first and/or second and/or third aspects except where such features are mutually exclusive.

According to a fifth aspect of the present invention there is provided an apparatus comprising an aqueous system which comprises an aqueous mixture of (a) a phosphonium compound and (b) a polymeric ammonium compound; wherein the weight ratio of compound (a) to compound (b) is from 0.2:1 to 20:1; and wherein
the phosphonium compound (a) has formula:

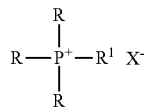

wherein each R is independently a $C_1$-$C_6$ alkyl group which is unsubstituted or substituted by a cyano, hydroxyl, esterified hydroxyl or aryl group;
$R^1$ represents a $C_8$-$C_{18}$ alkyl group which is substituted or unsubstituted; and
X represents either chlorine or bromine; and wherein
the polymeric ammonium compound (b) comprises the repeat unit:

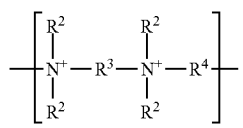

wherein each $R^2$ is independently a $C_1$-$C_2$ alkyl group which is substituted or unsubstituted;
$R^3$ represents a $C_2$-$C_{18}$ alkyl or alkenyl group which is substituted or unsubstituted; and
$R^4$ represents a $C_2$-$C_{18}$ alkyl or alkenyl group which is substituted or unsubstituted, a diethyl ether group, an isopropanol group, a N,N-dipropylurea group or a 2-butene group.

Suitably, the polymeric ammonium compound comprises n repeat units where n is from 2 to 40. Suitably n is 10-30. Suitably, n is 15-25. Suitably, n is 20. Suitably, the polymeric ammonium compound comprises sufficient counter-ions to balance the charge, Suitably, the counter-ions comprise singly charged ions, suitably halides. Suitably, the polymeric ammonium compound comprises 2n counter-ions. Suitably, the polymeric ammonium compound comprises chloride and/or bromide counter-ions.

Suitably, the polymeric ammonium compound (b) has formula:

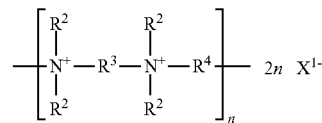

wherein each $R^2$ is independently a $C_1$-$C_2$ alkyl group which is substituted or unsubstituted;
$R^3$ represents a $C_2$-$C_{18}$ alkyl or alkenyl group which is substituted or unsubstituted;
$R^4$ represents a $C_2$-$C_{18}$ alkyl or alkenyl group which is substituted or unsubstituted, a diethyl ether group, an isopropanol group, a N,N-dipropylurea group or a 2-butene group;
$X^1$ represents either chlorine or bromine; and
n is 2-40.

Suitably, the apparatus comprises a cooling apparatus. Suitably, the apparatus comprises a pulping and/or papermaking apparatus. Suitably, the apparatus comprises oil and/or gas field apparatus.

Suitably, the apparatus comprises a cooling water system. Suitably, the apparatus comprises a pulping and/or papermaking water system. Suitably, the apparatus comprises an oil and/or gas field water system.

The aqueous system may comprise constituents other than water and compounds (a) and (b). The aqueous system may alternatively consist of water and compound (a) and (b). Suitably the aqueous system comprises a mixture of water, compounds (a) and (b) and other constituents. The aqueous system may contain oil. The aqueous system may comprise an oil and water emulsion.

Suitably, the weight ratio of compound (a) to compound (b) is from 0.2:1 to 20:1.

Suitably, the weight ratio of compound (a) to compound (b) is from 0.5:1 to 10:1. Suitably, the weight ratio of compound (a) to compound (b) is from 0.5:1 to 5:1. Suitably, the weight ratio of compound (a) to compound (b) is from 1:1 to 2:1. Suitably, the weight ratio of compound (a) to compound (b) is from 1:1 to 1.5:1, the weight ratio may for example be around 1.5:1. Suitably, the weight ratio of compound (a) to compound (b) is from 1.15:1 to 1.30:1, the weight ratio may for example be 1.25:1. The weight ratio of compound (a) to compound (b) may be from 2:1 to 5:1. The weight ratio of compound (a) to compound (b) may be from 2.5:1 to 4:1, the weight ratio may for example be around 4:1. The weight ratio of compound (a) to compound (b) may be from 3.1:1 to 3.5:1, the weight ratio may for example be 3.5:1

Suitably, the apparatus comprises an aqueous system comprising synergistic mixture of compounds (a) and (b). Suitably, by "synergistic mixture" it is meant that the mixture of compounds (a) and (b) has a synergistic effect on the inhibition of growth of one or more biological organisms, preferably micro-organisms such as bacteria, fungi and/or algae.

Suitably, the apparatus comprises an aqueous system comprising compound (a) and compound (b) in a combined amount of from 0.05 to 200 parts by weight per one million parts by weight of said aqueous system.

The apparatus may comprise an aqueous system comprising compound (a) and compound (b) in a combined amount of from 1 to 50 parts by weight per one million parts by weight of said aqueous system. Suitably, the apparatus comprises an aqueous system comprising compound (a) and compound (b) in a combined amount of from 2 to 30 parts by weight per one million parts by weight of said aqueous system.

The aqueous mixture may comprise one or more phosphonium compounds (a). Suitably, the aqueous system comprises a single type of phosphonium compound (a).

Suitably, the aqueous mixture comprises a phosphonium compound (a) having formula:

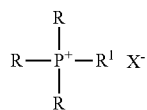

wherein each R is independently a $C_1$-$C_6$ alkyl group which is unsubstituted or substituted by a cyano, hydroxyl, esterified hydroxyl or aryl group;

$R^1$ represents a $C_8$-$C_{18}$ alkyl group; and

X represents either chlorine or bromine.

Suitably, each R is a $C_1$-$C_6$ alkyl group. Suitably, each R is a $C_3$-$C_5$ alkyl group. Suitably each R is a butyl group.

Suitably $R^1$ represents a $C_8$-$C_{18}$ alkyl group. Suitably, $R^1$ is a $C_{12}$-$C_{18}$ alkyl group. Suitably, $R^1$ is a tetradecyl group.

Suitably, X is chlorine.

Suitably, the aqueous mixture comprises tri n-butyl tetradecyl phosphonium chloride (hereafter "TTPC"). Suitably, compound (a) comprises TTPC. Suitably, compound (a) consists of TTPC.

The aqueous mixture may comprise one or more polymeric ammonium compounds (b). Suitably, the aqueous system comprises a single type of polymeric ammonium compound (b).

Suitably, the aqueous mixture comprises a polymeric ammonium compound (b) having formula:

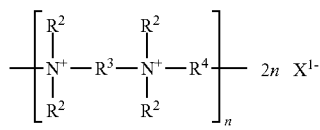

wherein each $R^2$ is independently a methyl group;

$R^3$ represents a $C_2$-$C_{12}$ alkyl group;

$R^4$ represents a $C_2$-$C_{12}$ alkyl group, a diethyl ether group, an isopropanol group or a N,N-dipropylurea group;

$X^1$ represents either chlorine or bromine; and n is 2-40.

Suitably, each $R^2$ is independently a methyl group.

Suitably, $R^3$ represents a $C_2$-$C_{12}$ alkyl group. Suitably, $R^3$ is a $C_2$-$C_4$ alkyl group. Suitably, $R^3$ is a $C_2$ alkyl group.

Suitably, $R^4$ represents a $C_2$-$C_{12}$ alkyl group, a diethyl ether group, an isopropanol group or a N,N-dipropylurea group. Suitably, $R^4$ represents a diethyl ether group.

Suitably, $X^1$ is chlorine.

Suitably, n is 10-30. Suitably, n is 15-25. Suitably, n is 20.

Suitably, the aqueous mixture comprises Poly[oxyethylene(dimethylimino)ethylene(dimethylimino)ethylene dichloride] (hereafter "polyquat").

Suitably, compound (b) comprises Poly[oxyethylene(dimethylimino)ethylene(dimethylimino)ethylene dichloride].

Suitably, compound (b) consists of Poly[oxyethylene(dimethylimino)ethylene(dimethylimino)ethylene dichloride].

The aqueous mixture may comprise α-4-[1-tris(2-hydroxyethyl)ammonium chloride-2-butenyl] poly[1-dimethylammonium chloride-2-butenyl]-ω-tris(2-hydroxyethyl)ammonium chloride.

Suitably, the apparatus comprises an aqueous system comprising a biocidal composition according to the first aspect.

The apparatus of the fifth aspect may comprise any feature as described in relation to the first and/or second and/or third and/or fourth aspect except where such features are mutually exclusive.

According to a sixth aspect of the present invention there is provided an apparatus comprising an aqueous system which comprises an aqueous mixture of (a) a phosphonium chloride compound and (b) a polymeric ammonium compound.

Suitably, the polymeric ammonium compound comprises a polymeric ammonium chloride compound.

Suitably, the apparatus comprises an aqueous system comprising an aqueous mixture of (a) tri-n-butyl n-tetradecyl phosphonium chloride (hereafter "TTPC") and (b) a polymeric ammonium chloride compound.

The polymeric ammonium compound (b) may comprise a compound having a formula as defined in relation to compound (b) in the first aspect. Suitably, the polymeric ammonium compound (b) comprises poly[oxyethylene(dimethylimino)ethylene(dimethylimino)ethylene dichloride. Alternatively, the polymeric ammonium compound (b) may comprise α-4-[1-tris(2-hydroxyethyl)ammonium chloride-2-butenyl]poly[1-dimethylammonium chloride-2-butenyl]-ω-tris(2-hydroxyethyl)ammonium chloride.

Suitably, the apparatus comprises a cooling apparatus. Suitably, the apparatus comprises a pulping and/or papermaking apparatus. Suitably, the apparatus comprises oil and/or gas field apparatus.

Suitably, the apparatus comprises a cooling water system. Suitably, the apparatus comprises a pulping and/or papermaking water system. Suitably, the apparatus comprises an oil and/or gas field water system.

The aqueous system may comprise constituents other than water and compounds (a) and (b). The aqueous system may alternatively consist of water and compound (a) and (b). Suitably the aqueous system comprises a mixture of water, compounds (a) and (b) and other constituents. The aqueous system may contain oil. The aqueous system may comprise an oil and water emulsion.

Suitably, the weight ratio of (a) to (b) is from 0.2:1 to 20:1.

Suitably, the weight ratio of compound (a) to compound (b) is from 0.5:1 to 10:1. Suitably, the weight ratio of compound (a) to compound (b) is from 0.5:1 to 5:1. Suitably, the weight ratio of compound (a) to compound (b) is from 1:1 to 2:1. Suitably, the weight ratio of compound (a) to compound (b) is from 1:1 to 1.5:1, the weight ratio may for example be around 1.5:1. Suitably, the weight ratio of compound (a) to compound (b) is from 1.15:1 to 1.30:1, the weight ratio may for example be 1.25:1. The weight ratio of compound (a) to compound (b) may be from 2:1 to 5:1, The weight ratio of compound (a) to compound (b) may be from 2.5:1 to 4:1, the weight ratio may for example be around 4:1.

The weight ratio of compound (a) to compound (b) may be from 3.1:1 to 3.5:1, the weight ratio may for example be 3.5:1.

Suitably, the apparatus comprises an aqueous system comprising compound (a) and compound (b) in a combined amount of from 0.05 to 200 parts by weight per one million parts by weight of said aqueous system.

The apparatus may comprise an aqueous system comprising compound (a) and compound (b) in a combined amount of from 1 to 50 parts by weight per one million parts by weight of said aqueous system. Suitably, the apparatus comprises an aqueous system comprising compound (a) and compound (b) in a combined amount of from 2 to 30 parts by weight per one million parts by weight of said aqueous system.

Suitably, the apparatus comprises a synergistic mixture of compounds (a) and (b).

Suitably, there is provided an apparatus comprising an aqueous system comprising an aqueous mixture of (a) tri-n-butyl n-tetradecyl phosphonium chloride (hereafter "TTPC") and (b) poly[oxyethylene(dimethylimino)ethylene (dimethylimino)ethylene dichloride (hereafter "polyquat"); and wherein the weight ratio of (a) to (b) is from 0.2:1 to 20:1.

Suitably, the apparatus comprises an aqueous system comprising a biocidal composition according to the second aspect.

The apparatus of the sixth aspect may comprise any feature as described in relation to the first and/or second and/or third and/or fourth and/or fifth aspect except where such features are mutually exclusive.

DETAILED DESCRIPTION OF PREFERRED EMBODIMENTS

The present invention will now be illustrated by way of example with reference to the following preferred embodiments.

Synergy

The exemplified embodiments illustrate the synergistic relationship obtained with the biocidal compositions of the present invention. Synergy was determined by the industry accepted method described by S. C. Kull et al. in *Applied Microbiology*, vol. 9, pages 538-541 (1961) using the relationship:

$$Q_a/Q_A + Q_b/Q_B = \text{synergy index}$$

Where:

$Q_A$ = quantity of composition A, acting alone, producing an end point $Q_B$ = quantity of composition B, acting alone, producing an end point $Q_a$ = quantity of composition A in mixture, producing an end point $Q_b$ = quantity of composition B in mixture, producing an end point <1, it indicates synergy If the synergy index (SI) is: 1, it indicates additivity >1, it indicates antagonism

Example 1

A suspension of *Pseudomonas aeruginosa* bacteria containing from 3-5×10$^6$ cells/mL was prepared in pH 8.5 phosphate buffer. Aliquots of this suspension were dosed with the indicated concentrations of the different compositions with the concentrations being measured as ppm by weight of the stated composition in the dosed suspension. At the designated contact times, each aliquot was sampled to determine the total number of viable organisms in colony forming units per milliliter (CFU/mL) on plate count agar. An endpoint of 1 or 4 $\log_{10}$ reduction in viable organisms was then selected for calculating synergy.

The following formulations (compositions C and D) according to the invention were prepared from:

Bellacide 350 (an aqueous composition of tri n-butyl n-tetradecyl phosphonium chloride (hereafter "TTPC") and water consisting of water and 50% by weight of TTPC) (composition A);

WSCP (an aqueous composition of poly[oxyethylene (dimethyliminio)ethylene(dimethyliminio)ethylene dichloride] (hereafter "poyquat") and water consisting of water and 60% by weight of polyquat); (composition B); and water The components were added sequentially in the proper amounts to yield the desired formulation starting with TTPC followed by polyquat and then water and were gently mixed to form a homogenous mixture.

Formulations:

Composition C (ratio A:B=4:1)

4 parts by weight composition A
1 part by weight composition B
5 parts by weight water Composition D (ratio A:B=1.5:1)

3 parts by weight composition A
2 parts by weight composition B
5 parts by weight water Activity of Compositions A to D Against *Pseudomonas aeruginosa*

| Composition | Concentration, ppm | Log$_{10}$ Reduction | | |
|---|---|---|---|---|
| | | 1 hour | 3 hours | 6 hours |
| A | 1.0 | 0 | 1.1 | 3.3 |
| | 2.0 | 1.1 | 4.7 | 5.3 |
| | 4.0 | 1.0 | 6.2 | 6.2 |
| | 8.0 | 0.7 | 6.2 | 6.2 |
| B | 0.8 | 0.1 | 1.0 | 2.1 |
| | 1.7 | 0.8 | 2.1 | 4.1 |
| | 3.3 | 1.5 | 6.2 | 6.2 |
| | 6.7 | 1.2 | 6.2 | 6.2 |
| C | 1.9 | 1.2 | 3.3 | 4.3 |
| | 3.8 | 1.1 | 3.9 | 5.3 |
| | 7.7 | 4.2 | 6.2 | 6.2 |
| | 15.4 | 4.0 | 6.2 | 6.2 |
| D | 1.9 | 2.0 | 5.0 | 5.0 |
| | 3.7 | 3.3 | 5.3 | 5.3 |
| | 7.4 | 5.0 | 6.2 | 6.2 |
| | 14.8 | 4.6 | 6.2 | 6.2 |

Synergy calculation for composition C:

After one hour of contact time, to achieve ≥1 $\log_{10}$ reduction, $Q_A$=2 (ppm A alone)
$Q_B$=3.3 (ppm B alone)
$Q_a$=0.76 (ppm A in mixture)
$Q_b$=0.19 (ppm B in mixture)

SI=0.76/2+0.19/3.3=0.44

Synergy calculation for composition D:

After one hour of contact time, to achieve a ≥1 $\log_{10}$ reduction, $Q_A$=2 (ppm A alone)
$Q_B$=3.3 (ppm B alone)

$Q_a$=0.57 (ppm A in mixture)
$Q_b$=0.38 (ppm B in mixture)

$$SI=0.57/2+0.38/3.3=0.41$$

Example 2

A suspension of *Pseudomonas aeruginosa* bacteria was prepared, dosed and sampled as described in Example 1. An endpoint of 1 or 4 $\log_{10}$ reduction in viable organisms was selected for calculating synergy.

The following formulations (products E to H) according to the invention were prepared from: Bellacide 350 (an aqueous composition of tri n-butyl n-tetradecyl phosphonium chloride (hereafter "TTPC") and water consisting of water and 50% by weight of TTPC) (composition A);

WSCP (an aqueous composition of poly[oxyethylene (dimethyliminio)ethylene(dimethyliminio)ethylene dichloride] (hereafter "poyquat") and water consisting of water and 60% by weight of polyquat) (composition B);

a hydrotrope composition consisting of an aqueous mixture of water and 70% by weight of alkyl iminodiopropionate amphoteric surfactant; and water.

Composition E (ratio A:B=4:1)

4 parts by weight composition A
1 part by weight composition B
1.82 parts by weight hydrotrope composition
3.18 parts by weight water Composition F (ratio A:B=1.5:1)

3 parts by weight composition A
2 parts by weight composition B
1.96 parts by weight hydrotrope composition
3.04 parts by weight water Composition G (ratio A:B=1:1)

2.5 parts by weight composition A
2.5 parts by weight composition B
2.1 parts by weight hydrotrope composition
2.9 parts by weight water Composition H (ratio A:B=1:1)

3.3 parts by weight composition A
3.3 parts by weight composition B
3.4 parts by weight hydrotrope composition Activity of compositions A and B and E to H against *Pseudomonas aeruginosa*

| Composition | Concentration, ppm | $\log_{10}$ Reduction | | |
|---|---|---|---|---|
| | | 1 hour | 3 hours | 6 hours |
| A | 1.0 | 0.1 | 0.9 | 1.8 |
| | 2.0 | 0.7 | 2.9 | 4.2 |
| | 4.0 | 4.1 | 6.6 | 6.5 |
| B | 0.8 | 1.4 | 1.6 | 1.6 |
| | 1.7 | 2.8 | 3.4 | 4.2 |
| | 3.3 | 4.7 | 6.6 | 6.5 |
| E | 1.9 | 4.4 | 6.6 | 6.6 |
| | 3.8 | 6.6 | 6.6 | 6.6 |
| | 7.7 | 6.6 | 6.6 | 6.6 |
| F | 1.9 | 6.6 | 6.6 | 6.6 |
| | 3.7 | 6.6 | 6.6 | 6.6 |
| | 7.4 | 6.6 | 6.6 | 6.6 |
| G | 1.8 | 4.7 | 6.6 | 6.5 |
| | 3.6 | 6.4 | 6.6 | 6.5 |
| | 7.3 | 6.4 | 6.6 | 6.5 |

-continued

| Composition | Concentration, ppm | $\log_{10}$ Reduction | | |
|---|---|---|---|---|
| | | 1 hour | 3 hours | 6 hours |
| H | 1.4 | 4.2 | 6.6 | 6.5 |
| | 2.7 | 5.4 | 6.6 | 6.5 |
| | 5.5 | 6.4 | 6.6 | 6.5 |

Synergy calculation for composition E:
After one hour of contact time, to achieve a ≥4 $\log_{10}$ reduction,
$Q_A$=4 (ppm A alone)
$Q_B$=3.3 (ppm B alone)
$Q_a$=0.76 (ppm A in mixture)
$Q_b$=0.19 (ppm B in mixture)

$$SI=0.76/4+0.19/3.3=0.25$$

Synergy calculation for composition F:
After one hour of contact time, to achieve a ≥4 $\log_{10}$ reduction,
$Q_A$=4 (ppm A alone)
$Q_B$=3.3 (ppm B alone)
$Q_a$=0.57 (ppm A in mixture)
$Q_b$=0.38 (ppm B in mixture)

$$SI=0.57/4+0.38/3.3=0.26$$

Synergy calculation for composition G:
After one hour of contact time, to achieve a ≥4 $\log_{10}$ reduction,
$Q_A$=4 (ppm A alone)
$Q_B$=3.3 (ppm B alone)
$Q_a$=0.45 (ppm A in mixture)
$Q_b$=0.45 (ppm B in mixture)

$$SI=0.45/4+0.45/3.3=0.25$$

Synergy calculation for composition H:
After one hour of contact time, to achieve a ≥4 $\log_{10}$ reduction,
$Q_A$=4 (ppm A alone)
$Q_B$=3.3 (ppm B alone)
$Q_a$=0.47 (ppm A in mixture)
$Q_b$=0.47 (ppm B in mixture)

$$SI=0.47/4+0.47/3.3=0.26$$

Example 3

A suspension of *Chlorella vulgaris* algae that had an absorbance of 0.5 at 450 nm was prepared in pH 8.5 Allen's media. This gives the appropriate number of algae cells per milliliter for the biocide challenge test. One hundred and fifty microliters of this suspension was placed into each well of a 96 well tissue culture plate. The first well in each row was dosed with the desired amount of the indicated product and the final volume was brought up to 300 microliters using the algae suspension. Serial two fold dilutions were then made down each row. The plates were incubated under cool white lights for 12 days and then the minimum inhibitory concentration was determined. Synergy was calculated based on a comparison of the minimum inhibitory concentration achieved by each composition.

Activity of compositions A and B and E to H against *Chlorella vulgaris*

Minimum Inhibitory Concentration (in ppm)

Evaluation—Test Rows

| Composition | 1 | 2 | Average |
|---|---|---|---|
| A | 4 | 4 | 4 |
| B | 6.7 | 13.3 | 10 |
| E | 15.4 | 15.4 | 15.4 |
| F | 29.6 | 14.8 | 22.2 |
| G | 29 | 1629 | 29 |
| H | 21.8 | 21.8 | 21.8 |

Synergy calculation for composition E:
$Q_A$=4 (ppm A alone)
$Q_B$=10 (ppm B alone)
$Q_a$=6.2 (ppm A in mixture)
$Q_b$=1.5 (ppm B in mixture)

$$SI=6.2/4+1.5/10=1.70$$

Synergy calculation for composition F:
$Q_A$=4 (ppm A alone)
$Q_B$=10 (ppm B alone)
$Q_a$=6.3 (ppm A in mixture)
$Q_b$=4.4 (ppm B in mixture)

$$SI=6.3/4+4.4/10=2.02$$

Synergy calculation for composition G:
$Q_A$=4 (ppm A alone)
$Q_B$=10 (ppm B alone)
$Q_a$=7.3 (ppm A in mixture)
$Q_b$=7.3 (ppm B in mixture)

$$S1=7.314+7.3/10=2.56$$

Synergy calculation for composition H:
$Q_A$=4 (ppm A alone)
$Q_B$=10 (ppm B alone)
$Q_a$=7.3 (ppm A in mixture)
$Q_b$=7.3 (ppm B in mixture)

$$SI=7.3/4+7.3/10=2.56$$

It can be seen from Example 3 that the testedcompositions did not show synergy in relation to inhibition of growth of *Chlorella vulgaris* algae. However compositions that did not exhibit synergy in relation to inhibition of growth of *Chlorella vulgaris* algae remained effective against such growth and also exhibited significant synergy in relation to growth of *Pseudomonas aeruginosa* bacteria as illustrated by Example 2.

It will be appreciated that preferred embodiments of the present invention may prove particularly effective in treating water systems and in particular in inhibiting growth of organisms such as *Pseudomonas aeruginosa* bacteria. Compositions in which the ratio of TTPC:polyquat is selected to be around 1.5:1 may be particularly effective against both *Chlorella vulgaris* algae and *Pseudomonas aeruginosa* bacteria.

The invention claimed is:

1. A biocidal composition comprising an aqueous mixture of (a) a phosphonium compound and (b) a polymeric ammonium compound; wherein the weight ratio of compound (a) to compound (b) is from 0.5:1 to 5:1; and wherein the phosphonium compound (a) is tri n-butyl n-tetradecyl phosphonium chloride (hereinafter "TTPC"); and wherein the polymeric ammonium compound (b) has formula:

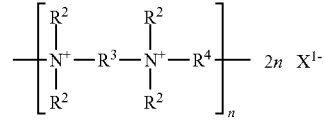

wherein each $R^2$ is independently a methyl group;
$R^3$ represents a $C_2$ alkyl group;
$R^4$ represents a diethyl ether group or an isopropanol group;
$X^1$ represents chlorine; and
n is 2-40; and
wherein the composition comprises an amphoteric surfactant.

2. A composition according to claim 1, wherein compound (b) is Poly[oxyethylene(dimethylimino)ethylene(dimethylimino)ethylene dichloride] (hereafter "polyquat").

3. The composition according to claim 1, wherein the weight ratio of compound (a) to compound (b) is from 1:1 to 2:1.

4. A composition according to claim 1, wherein the biocidal composition has a synergy index (SI) of less than 1 in relation to the effect of the composition on the inhibition of growth of *Pseudomonas aeruginosa* bacteria, wherein the synergy index is determined by:

$$Q_a/Q_A+Q_b/Q_B=\text{synergy index(SI)}$$

wherein:
$Q_A$=quantity of compound (a), acting alone, producing an end point
$Q_B$=quantity of compound (b), acting alone, producing an end point
$Q_a$=quantity of compound (a) in mixture, producing an end point
$Q_b$=quantity of compound (b) in mixture, producing an end point.

5. A composition according to claim 1, wherein the composition comprises compound (a) and compound (b) in a combined amount of between 1% and 100% by weight of the composition.

6. A method of treating an aqueous system to inhibit growth of one or more micro-organisms therein; wherein the method comprises adding (a) a phosphonium compound and (b) a polymeric ammonium compound to an aqueous system such that the weight ratio of compound (a) to compound (b) is from 0.5:1 to 5:1; and wherein
the phosphonium compound (a) is tri n-butyl n-tetradecyl phosphonium chloride (hereinafter "TTPC"); and wherein the polymeric ammonium compound (b) has formula:

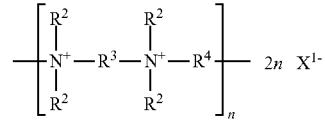

wherein each $R^2$ is independently a methyl group;
$R^3$ represents a $C_2$ alkyl group;

R⁴ represents a diethyl ether group or an isopropanol group;
X¹ represents chlorine; and
n is 2-40; and
wherein the method comprises adding an amphoteric surfactant.

7. The method according to claim 6, wherein compound (b) is Poly[oxyethylene(dimethylimino)ethylene(dimethylimino)ethylene dichloride] (hereafter "polyquat").

8. The method according to claim 6, wherein the weight ratio of compound (a) to compound (b) is from 1:1 to 2:1.

9. The method according to claim 6 wherein the method comprises adding compound (a) and compound (b) to the aqueous system such that they are present in a combined amount of from 0.05 to 200 parts by weight per one million parts by weight of said aqueous system.

10. The method according to claim 6, wherein the method comprises: adding a biocidal composition comprising an aqueous mixture of (a) the phosphonium compound and (b) the polymeric ammonium compound to the aqueous system wherein the weight ratio of compound (a) to compound (b) in the biocidal composition is from 0.5:1 to 5:1.

11. The method according to claim 6, wherein the method comprises a method of controlling the growth of *Pseudomonas aeruginosa* bacteria and/or *Chlorella vulgaris* algae in an aqueous system.

12. A method according to claim 6, wherein the aqueous system comprises a cooling water system, a pulping and/or papermaking water system or an oil and/or gas field water system.

13. An apparatus comprising an aqueous system which comprises (a) a phosphonium compound and (b) a polymeric ammonium compound; wherein the weight ratio of compound (a) to compound (b) is from 0.5:1 to 5:1; and wherein
the phosphonium compound (a) is tri n-butyl n-tetradecyl phosphonium chloride (hereinafter "TTPC"); and
wherein the polymeric ammonium compound (b) has formula:

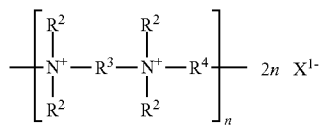

wherein each R² is independently a methyl group;
R³ represents a C₂ alkyl group;
R⁴ represents a diethyl ether group or an isopropanol group;
X¹ represents chlorine; and
n is 2-40; and
wherein the aqueous system comprises an amphoteric surfactant.

14. The apparatus of claim 13, wherein compound compound (b) is Poly[oxyethylene(dimethylimino)ethylene(dimethylimino)ethylene dichloride] (hereafter "polyquat").

15. The apparatus of claim 13 wherein the weight ratio of compound (a) to compound (b) is from 1:1 to 2:1.

16. The apparatus of claim 13 wherein the aqueous system comprises compound (a) and compound (b) in a combined amount of from 0.05 to 200 parts by weight per one million parts by weight of said aqueous system.

17. The apparatus according to claim 13, wherein the aqueous system comprises a biocidal composition comprising an aqueous mixture of (a) the phosphonium compound and (b) the polymeric ammonium compound wherein the weight ratio of compound (a) to compound (b) in the biocidal composition is from 0.5:1 to 5:1.

18. The apparatus of claim 13, wherein the apparatus comprises a cooling apparatus, pulping and/or papermaking apparatus or oil and/or gas field apparatus.

19. A composition according to claim 1, wherein the amphoteric surfactant is selected from the group consisting of alkyl ampho- or iminocarboxylate amphoteric surfactants and alkyl ampho- or iminodicarboxylate amphoteric surfactants.

20. A composition according to claim 1, wherein the amphoteric surfactant is selected from the group consisting of alkyl iminodipropionate amphoteric surfactants.

21. A composition according to claim 20, wherein the biocidal composition comprises an alkyl iminodipropionate amphoteric surfactant in an amount of between 0.3% and 35% by weight.

22. A method according to claim 6, wherein the amphoteric surfactant is selected from the group consisting of alkyl ampho- or iminocarboxylate amphoteric surfactants and alkyl ampho- or iminodicarboxylate amphoteric surfactants.

23. A method according to claim 6, wherein the amphoteric surfactant is selected from the group consisting of alkyl iminodipropionate amphoteric surfactants.

24. An apparatus according to claim 13, wherein the amphoteric surfactant is selected from the group consisting of alkyl ampho- or iminocarboxylate amphoteric surfactants and alkyl ampho- or iminodicarboxylate amphoteric surfactants.

25. An apparatus according to claim 13, wherein the amphoteric surfactant is selected from the group consisting of alkyl iminodipropionate amphoteric surfactants.

* * * * *